(12) United States Patent
Walton, III (10) Patent No.: US 8,608,078 B2
(45) Date of Patent: Dec. 17, 2013

(54) ELECTRONIC MEDICAL INFORMATION CARD AND SYSTEM AND METHOD OF USE

(76) Inventor: James F. Walton, III, Tallahassee, FL (US)

(*) Notice: Subject to any disclaimer, the term of this patent is extended or adjusted under 35 U.S.C. 154(b) by 0 days.

(21) Appl. No.: 13/477,720

(22) Filed: May 22, 2012

(65) Prior Publication Data

US 2012/0303387 A1 Nov. 29, 2012

Related U.S. Application Data (63) Continuation-in-part of application No. 13/114,773, filed on May 24, 2011, now Pat. No. 8,308,062.

(51) Int. Cl.
*G06K 19/00* (2006.01)

(52) U.S. Cl.
USPC .......................................................... 235/487

(58) Field of Classification Search
USPC .......................................................... 235/487
See application file for complete search history.

(56) References Cited

U.S. PATENT DOCUMENTS

| | | | |
|---|---|---|---|
| 5,658,016 A | 8/1997 | Goeken | |
| D426,833 S | 6/2000 | Vanelli | |
| 6,513,720 B1 | 2/2003 | Armstrong | |
| 6,747,561 B1 | 6/2004 | Reeves | |
| 6,751,805 B1 * | 6/2004 | Austion | 2/94 |
| 6,845,063 B2 | 1/2005 | Mitchell | |
| 7,827,043 B2 | 11/2010 | Tahan | |
| 8,308,062 B1 * | 11/2012 | Walton, III | 235/380 |
| 2002/0120470 A1 | 8/2002 | Trice, Sr. | |
| 2003/0058110 A1 | 3/2003 | Rich | |
| 2003/0101077 A1 | 5/2003 | Wohl | |
| 2003/0150143 A1 | 8/2003 | Hazard | |
| 2005/0194270 A1 | 9/2005 | Gombar | |
| 2006/0010012 A1 | 1/2006 | Franzblau et al. | |
| 2006/0015368 A1 | 1/2006 | Hockey | |
| 2006/0085226 A1 | 4/2006 | Kamber | |
| 2006/0142057 A1 | 6/2006 | Schuler et al. | |
| 2007/0158411 A1 | 7/2007 | Krieg, r. | |
| 2007/0265884 A1 | 11/2007 | Lubell et al. | |
| 2008/0126729 A1 | 5/2008 | Cai et al. | |
| 2008/0319798 A1 | 12/2008 | Kelley | |
| 2009/0076849 A1 | 3/2009 | Diller | |
| 2009/0101721 A1 | 4/2009 | Hawthorne et al. | |
| 2009/0295569 A1 | 12/2009 | Corwin et al. | |
| 2010/0115609 A1 | 5/2010 | Spence | |

* cited by examiner

*Primary Examiner* — Christle Marshall
(74) *Attorney, Agent, or Firm* — The Livingston Firm; Edward M. Livingston, Esq.; Bryan L. Loeffler, Esq.

(57) ABSTRACT

An electronic medical information card (1) for storing an individual's emergency medical information on. The medical information card is stored in a storage sleeve (2) to attract the attention of medical personnel. The storage sleeve may be removably attachable to a user's driver's license, wallet, purse and so forth so that it may be easily seen by a first responder. The information on the electronic medical information card may be updated by an individual over the internet by sending updated information to a central location that updates the information in a central database and allows the user to download the updated information back onto the electronic medical information card. The electronic medical information card may also be used in conjunction with an Advanced Automatic Collision Notification system or GPS system to alert emergency personnel of the location of an emergency and to relay medical information.

18 Claims, 6 Drawing Sheets

ELECTRONIC MEDICAL INFORMATION CARD AND SYSTEM AND METHOD OF USE

CROSS-REFERENCE TO RELATED APPLICATIONS

This application is a continuation-in-part of application Ser. No. 13/114,773, filed on May 24, 2011, which is currently pending. The patent application identified above is incorporated herein by reference in its entirety to provide continuity of disclosure.

FIELD OF THE INVENTION

This invention relates to providing personal medical information to first responders during an emergency through the use of electronic storage devices and the internet.

BACKGROUND OF THE INVENTION

During a medical emergency, time is of the essence for a patient to receive the proper care from first responders. In such instances it is important that first responders are aware of a patient's medical history including allergies to drugs, current medications and medical conditions. It also becomes necessary to have the patient's emergency contact information and physician contact information. In many instances patients are unconscious and unable to provide any information to first responders. Conventional methods of providing such information include medical identification bracelets which may list an individual's allergies or medical conditions. However, only a limited amount of information can be included on such bracelets. There have also been attempts to store an individual's medical information on electronic storage devices such as flash drives or radio frequency identification cards ("RFID") in the past. However, many of these devices are complicated to use and to store information on. In addition, many of these devices are carried in wallets or on key chains and can easily be missed by a first responder. In addition, such devices may be damaged in certain situations, such as if the devices become wet during a medical emergency involving water or if the devices are near flames. A further problem with conventional devices occurs if an individual is injured in a foreign country, thereby rendering the electronic storage device useless because the information stored on the device is not written in the first responder's native language.

Therefore, the need exists for a personal medical information card and system and method of use that allows a user to easily store medical information on the card, has a card that is easily identifiable by a first responder as being a medical information card, is protectable from water and fire and allows a foreign language speaking first responder to read the information stored on the card.

The relevant prior art includes the following references:

| Pat. No. (U.S. Patent References) | Inventor | Issue/Publication Date |
|---|---|---|
| 7,827,043 | Tahan | Nov. 02, 2010 |
| 2010/0115609 | Spence | May 06, 2010 |
| 2009/0295569 | Corwin et al. | Dec. 03, 2009 |
| 2009/0101721 | Hawthorne et al. | Apr. 23, 2009 |
| 2009/0076849 | Diller | Mar. 19, 2009 |
| 2008/0126729 | Cai et al. | May 29, 2008 |
| 2008/0319798 | Kelley | Dec. 25, 2008 |
| 2007/0265884 | Lubell et al. | Nov. 15, 2007 |
| 2007/0158411 | Krieg, Jr. | Jul. 12, 2007 |
| 2006/0142057 | Schuler et al. | Jun. 29, 2006 |
| 2006/0085226 | Kamber | Apr. 20, 2006 |
| 2006/0015368 | Hockey | Jan. 19, 2006 |
| 2006/0010012 | Franzblau et al. | Jan. 12, 2006 |
| 2005/0194270 | Gombar | Sep. 08, 2005 |
| 6,845,063 | Mitchell | Jan. 18, 2005 |
| 6,751,805 | Austion | Jun. 22, 2004 |
| 6,747,561 | Reeves | Jun. 08, 2004 |
| 2003/0150143 | Hazard | Aug. 14, 2003 |
| 2003/0101077 | Whol | May 29, 2003 |
| 2003/0058110 | Rich | Mar. 27, 2003 |
| 6,513,720 | Armstrong | Feb. 04, 2003 |
| 2002/0120470 | Trice, Sr. | Aug. 29, 2002 |
| D426,833 | Vanelli | Jun. 20, 2000 |
| 5,658,016 | Goeken | Aug. 19, 1997 |
| 5,659,741 | Eberhardt | Aug. 19, 1997 |
| 5,337,290 | Ventimiglia et al. | Aug. 09, 1994 |
| 5,171,039 | Dusek | Dec. 15, 1992 |
| 4,575,127 | Michel | Mar. 11, 1986 |
| 4,491,725 | Pritchard | Jan. 01, 1985 |
| 4,318,554 | Anderson et al. | Mar. 09, 1982 |
| 3,792,542 | Cohan | Feb. 19, 1974 |

SUMMARY OF THE INVENTION

The primary object of the present invention is to provide an electronic medical information card and system and method of use that allows a user to easily store personal and medical information on the card.

Another object of the present invention is to provide an electronic medical information card that is easily identifiable by a first responder as being a medical information card.

An additional object of the present invention is to provide an electronic medical information card and system and method of use that is protectable from water and fire.

Another object of the present invention is to provide an electronic medical information card that may be used in conjunction with an Advanced Automatic Collision Notification system or GPS system to alert emergency personnel of the location of an emergency and to relay medical information.

The present invention fulfills the above and other objects by providing an electronic medical information card for storing emergency medical information, such as blood type, allergies, medical conditions, present medications, age, doctor information and emergency contact information. The card is preferably a secure digital ("SD") card or other electronic smart card having an electronic storage means. The card is stored in a brightly colored storage sleeve to attract the attention of medical personnel. The sleeve is removably attachable to a user's driver's license, wallet, purse and so forth so that it may be easily seen by a first responder. In addition, the storage sleeve is water proof and fire resistant to protect the electronic medical information card from becoming damaged. The information on the electronic medical information card may be updated by an individual over the internet by sending updated information to a central location that updates the information in a central database and allows the user to download the updated information back onto the electronic medical information card. An additional feature of the card allows a first responder to translate the information stored on the electronic medical information card into the first responder's native language.

The above and other objects, features and advantages of the present invention should become even more readily apparent

BRIEF DESCRIPTION OF THE DRAWINGS

In the following detailed description, reference will be made to the attached drawings in which.

DESCRIPTION OF THE PREFERRED EMBODIMENTS

Figure 1:
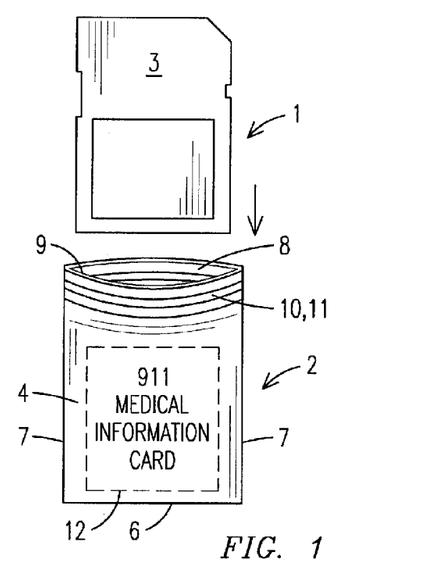
FIG. 1 is a front view of an electronic medical information card and storage sleeve of the present invention.
Figure 2:
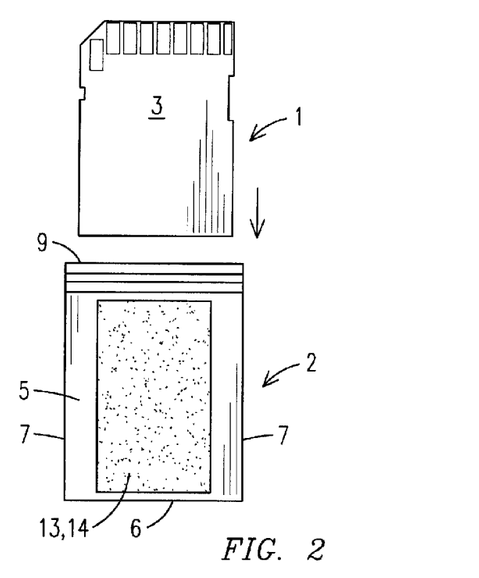
FIG. 2 is a rear view of an electronic medical information card and storage sleeve of the present invention.

With reference to FIGS. 1 and 2, a front view and a rear view, respectively, of an electronic medical information card 1 and storage sleeve 2 of the present invention is shown. The electronic medical information card 1 allows an individual to store emergency medical information, such as blood type, allergies, medical conditions, present medications, age, doctor information and emergency contact information. The medical information card is preferably a secure digital ("SD") card 3 or other electronic smart card having an electronic storage means, such as a radio-frequency identification ("RFID") chip. The medical information card 1 is stored in a storage sleeve 2 comprising a front panel 4 attached to a rear panel 5 along a bottom edge 6, and two side edges 7. An opening 8 is locate along a top edge 9 of the storage sleeve 2 for inserting the electronic 4 medical information card 1 through. A sealing means 10, such as adhesive 11, zip lock and so forth, is located along the opening 8 to seal the storage sleeve 2 shut. The storage sleeve 2 is preferably brightly colored to attract the attention of medical personnel and has a label portion 12 that informs a first responder that a medical information card 1 is inside the storage sleeve 2. The storage sleeve 2 may be removably attachable via an attachment means 13, such as an adhesive 14, to a user's driver's license, wallet, purse and so forth so that it may be easily seen by a first responder when a first responder goes to retrieve a patients driver's license. In addition, the storage sleeve 2 is preferably water proof and fire resistant to protect the medical information card 1 from becoming damaged if a patient is exposed to water and/or fire.

Figure 3:
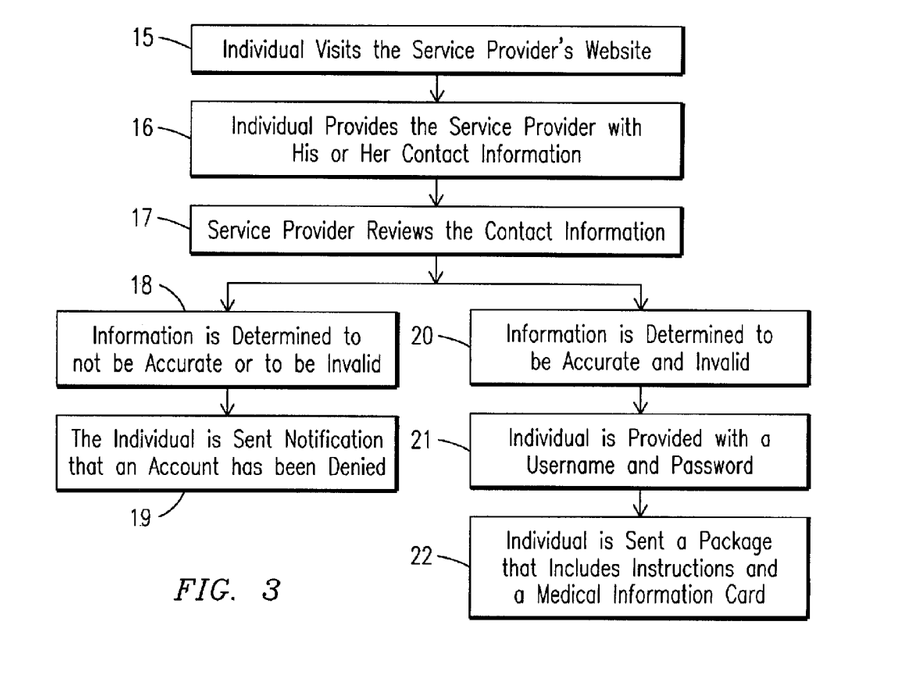
FIG. 3 is a flow chart showing an individual signing up for an account with a service provider that provides a medical information card to the individual.

With reference to FIG. 3, a flow chart showing an individual signing up for an account with a service provider that provides a medical information card to the individual. First, the individual visits the service provider's website 15. Then, the individual provides the service provider with his or her contact information, which includes the individual's name, address, phone number, email address and so forth 16. The service provider then reviews the contact information to determine the accuracy of the information and the validity of the information 17. If the information is determined to not be accurate or to be invalid 18, then the individual is sent notification, preferably via email, that an account has been denied 19. If the information is determined to be accurate and valid 20, then the individual is sent an approval, preferably via email, that an account has been created and the individual is provided with a username and password 21. Next, the individual is sent a package that includes instructions and a medical information card 22.

Figure 4:
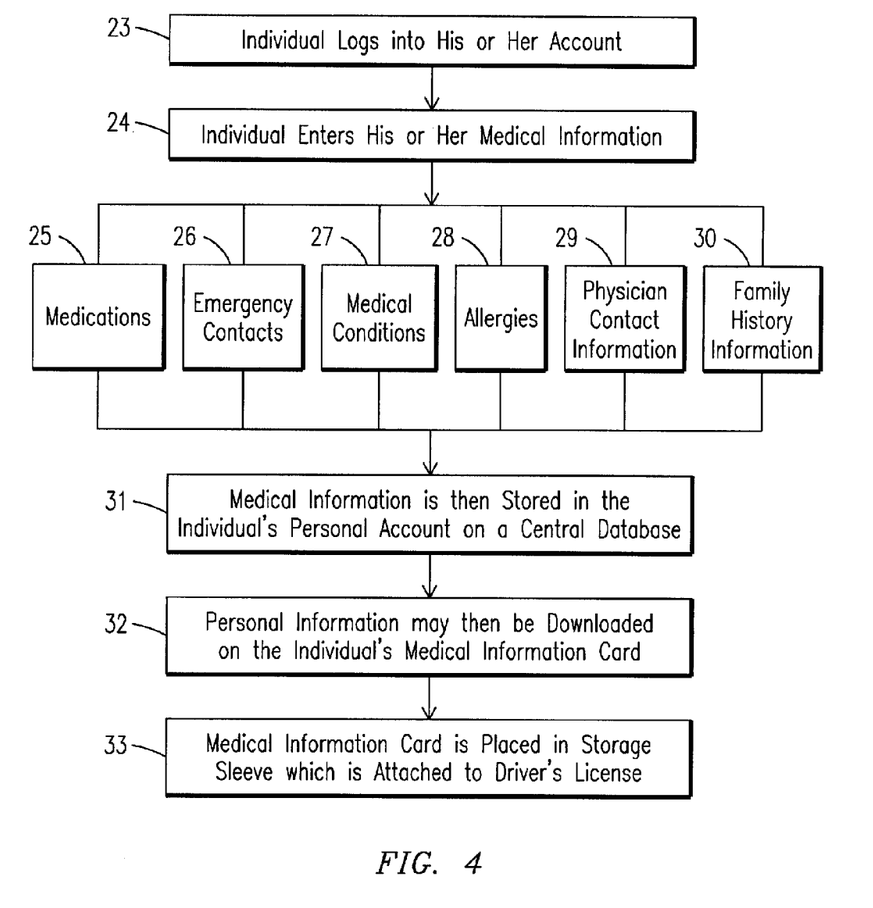
FIG. 4 is a flow chart showing the system and method of the present invention in which an individual enters medical information into an online account.

With reference to FIG. 4, a flow chart showing the system and method of the present invention in which an individual enters medical information into an online account is shown. First, the individual logs into his or her account using the username and password provided by the service provider 23. Then, the individual enters his or her medical information 24, which includes medications 25, emergency contacts 26, medical conditions 27, allergies 28, physician contact information 29, family history information 30 and so forth. The medical information is then stored in the individual's personal account on a central database 31. The medical information may then be downloaded on the individual's medical information card 32 by downloading a zip file, which may be encrypted, containing the medical information and copying it onto the medical information card. The individual may then attach a storage sleeve to his or her license, wallet, purse and so forth, insert the medical information card into the storage sleeve and seal the storage sleeve 33.

Figure 5:
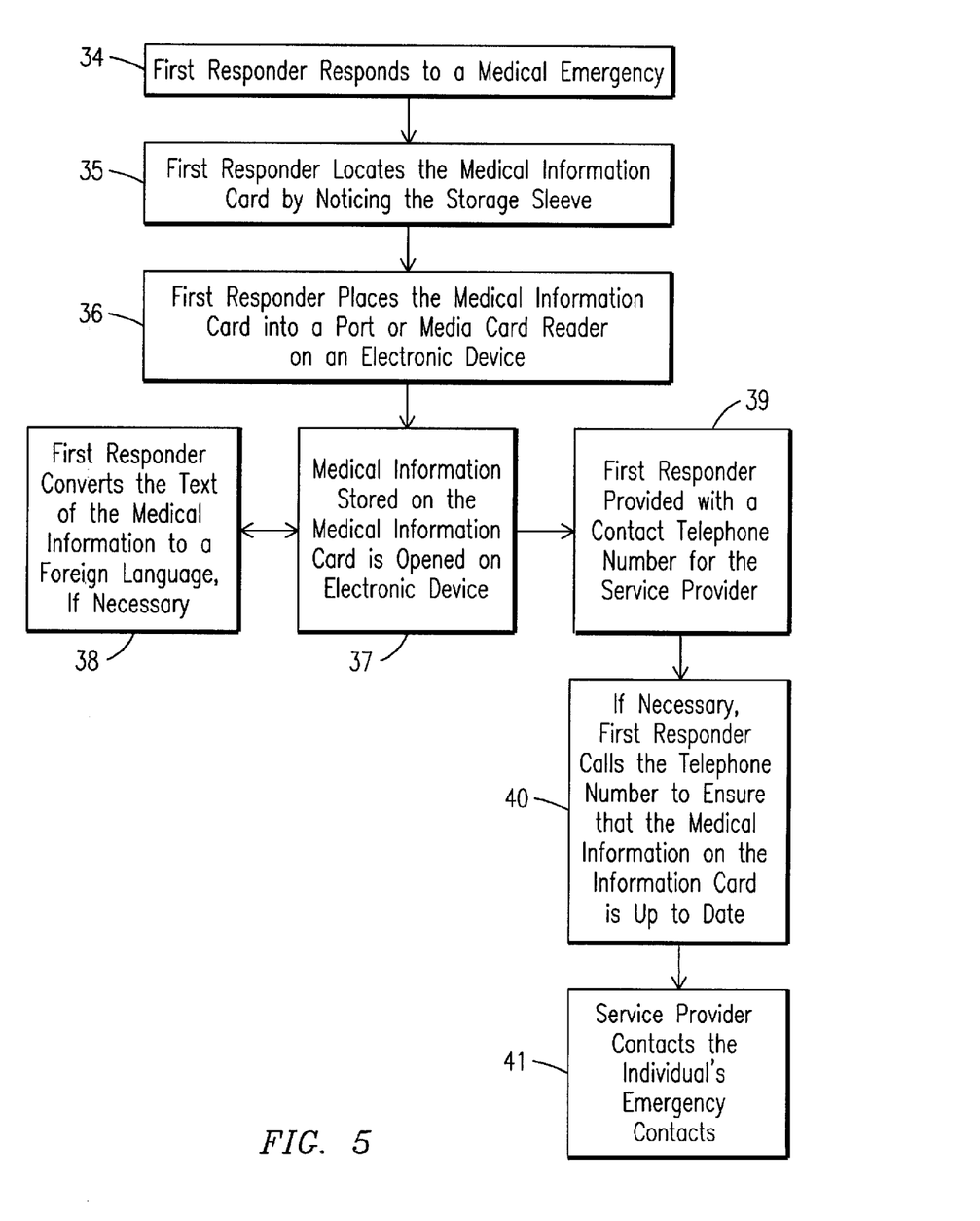
FIG. 5 is a flow chart showing the system and method of the present invention in which a first responder retrieves medical information from a patient's medical information card.

With reference to FIG. 5, a flowchart showing the system and method of the present invention in which a first responder retrieves medical information from a patient's medical information card is shown. First, a first responder responds to a medical emergency 34. Then, the first responder locates the medical information card by noticing the storage sleeve 35. Next, the first responder places the medical information card into a port or media card reader on an electronic device, such as a laptop or tablet 36. Then, the medical information stored on the medical information card is opened and the first responder may read and/or print the medical information 37. The first responder may also convert the text of the medical information to a foreign language if the patient has been injured in a foreign country 38. The first responder will also be provided with a contact telephone number for the service provider 39. In addition, the service provider will be able to tell when the information on the card was last updated. The first responder may call the telephone number if necessary to ensure that the medical information on the medical information card is up to date with the most current medical information stored on the central data base 40. In addition, after being notified of a medical emergency the service provider will contact the individual's emergency contacts to inform them of the medical emergency 41.

Figure 6:
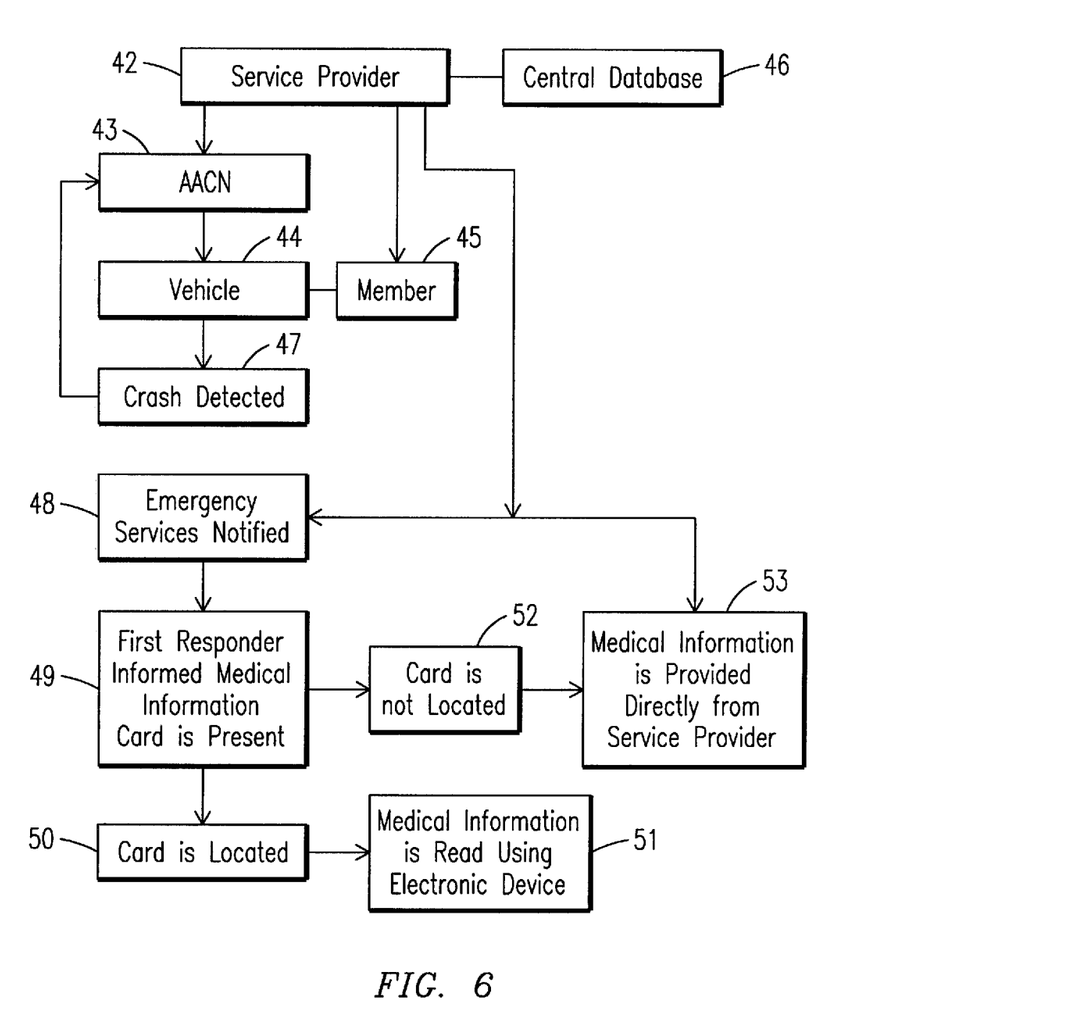
FIG. 6 is a flowchart showing the system and method of the present invention integrated into an Advanced Automatic Collision Notification ("AACN")

With reference to FIG. 6, a flowchart showing the system and method of the present invention integrated into an Advanced Automatic Collision Notification ("AACN") is illustrated. AACN is also known as Advanced Automatic Crash Notification or an Automatic Collision Notification. AACN is found on a number of motor vehicles and is used to alert emergency services that a crash has occurred in order to automatically summon assistance after a crash has occurred. AACN uses various sensors, such as airbag deployment, seatbelt pretensioners and so forth, to determine if a crash has occurred. After a crash has been detected, AACN will initiate a call to local 911 operators to deliver the vehicle's GPS location, crash-related data and to open a voice communications channel to the emergency call center. Conventional AACN is capable of determining crash-severity (including: speed, delta velocity, number of occupants and rollover data) as collected by in-vehicle sensors. This additional data is then used by emergency services providers to determine the quantity and type of rescue equipment that should be dispatched. However, conventional AACN does not provide medical information to emergency personnel and first responders. Under the present invention, the service provider 42 may also provide AACN services 43 and monitor vehicles 44 owned by individual's who are members 45 of service provider 42 and have an account with the service provider 42 and have a medical information card with medical information stored in the service provider's central database 46. If a crash is detected 47 via AACN 43, then emergency services are contacted by the service provider 48 and given the location of the vehicle using GPS. Emergency services are also notified that the occupant or occupants of the vehicle are members and medical information cards should be present at the crash scene 49. The medical information cards may be carried on an individual in his or her wallet or stored in the vehicle in a visible place such as on the dashboard near the vehicle identification number where a storage means, such as a storage sleeve, clip and so forth may be removably attached to the dashboard or integrated into the dashboard. The medical information card is then located by then located a first responder 50 and the medical information stored on the medical information card is opened on an electronic device 51. If the medical information card is not located 52, then the service provider may retrieve the occupant's or occupants' medical information from the central database and provide the medical information to the first responder 53. Alternatively, the service provider may provide the occupant's or occupants' medical information to the first responder prior to the first responder arriving on scene to save time.

Figure 7:
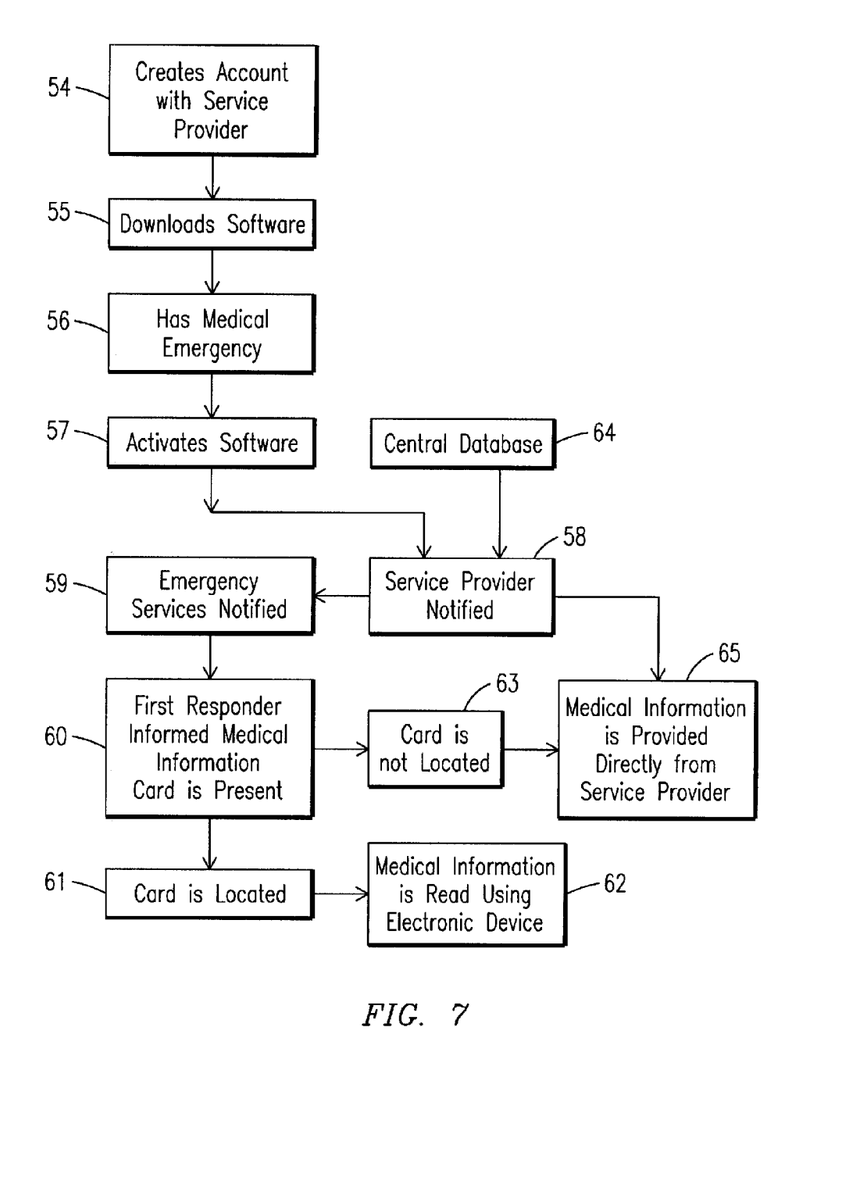
FIG. 7 is a flowchart showing the system and method of the present invention wherein a personal electronic device is used to alert the service provider of a medical emergency.

With reference to FIG. 7, a flowchart showing the system and method of the present invention wherein a personal electronic device is used to alert the service provider of a medical emergency is illustrated. After an individual creates an account with the service provider 54, the individual may download software onto an electronic device 55 having GPS, such as a smart phone, tablet and so forth. When the individual has a medical emergency 56, the individual may activate the software 57. For example, an individual may press an icon on the screen of the electronic device to activate the software. The software then sends an alert to the service provider that the individual needs medical assistance with the individual's location using GPS 58. Then, emergency services are contacted by the service provider 59 and given the location of the individual. Emergency services are also notified that the individual is a member and a medical information card should be present at the emergency scene 60. The medical information card is then located by then located a first responder 61 and the medical information stored on the medical information card is opened an electronic device 62 carried by the first responder. If the medical information card is not located 63, then the service provider may retrieve the individual's medical information from the central database 64 by contacting the service provider or by using the individual's electronic device and software downloaded thereon to access the information 66. Alternatively, the service provider may provide the individual's medical information to the first responder prior to the first responder arriving on scene to save time. The individual's electronic device may also be the medical information card itself that has integrated GPS and cellular communication and/or wifi communication. Alternatively, the medical information card may have a radio transmitter that sends a wireless signal to a base that is hooked into a phone line or cable line in the individual's home. The individual would send a signal that there is an emergency by simply pushing a button on the medical information card. The service provider would then know the location of the individual by using the GPS coordinates transmitted via cellular communication or wifi or by the location of the base. Then steps 59-65 would be carried out.

Figure 8:
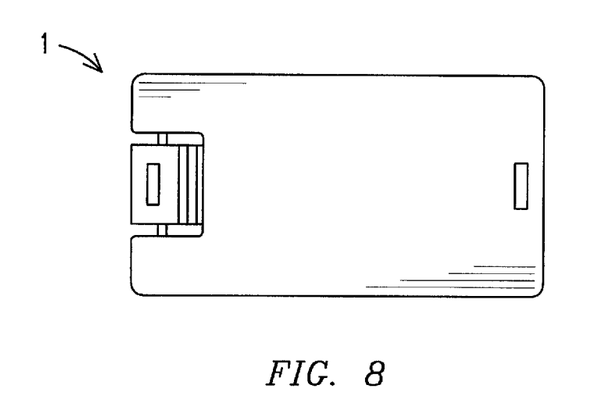
FIG. 8 is a front view of a medical information card of the present invention in a closed position.
Figure 9:
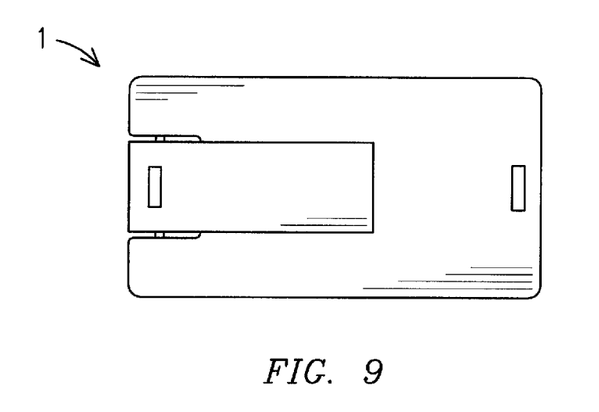
FIG. 9 is a rear view of a medical information card of the present invention in a closed position.
Figure 10:
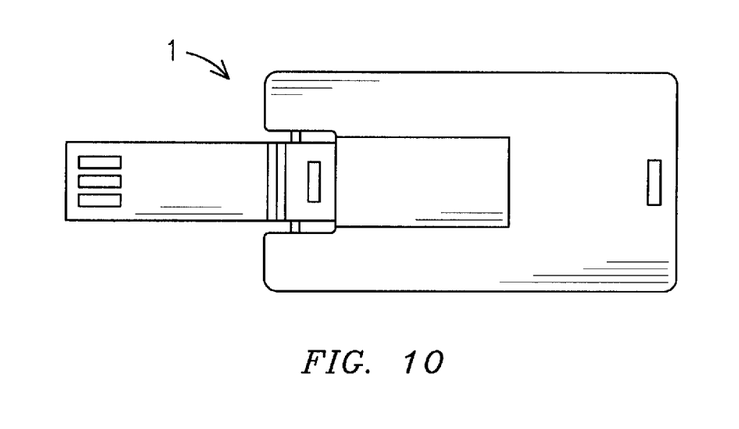
FIG. 10 is a rear view of a medical information card of the present invention in an open position.

Finally with reference to FIGS. 8 and 9, a front view and rear view, respectively, of a medical information card 1 of the present invention in a closed position is illustrated. With reference to FIG. 10, a rear view of a medical information card 1 of the present invention in an open position is illustrated. As illustrated here the, the medical information card 1 is a USB thumb drive 66 that may be opened and plugged into a USB port of an electronic device to access the medical information stored thereon.

It is to be understood that while a preferred embodiment of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

Having thus described my invention, I claim:

1. A method for using a medical information card for storing medical information and providing medical information to first responders comprising the steps of:
   a. an individual creating an account with a service provider over the internet;
   b. the individual providing the service provider with his or her contact information;
   c. the service provider reviewing the contact information and rendering a decision on whether to allow the individual to have an account;
   d. the service provider deciding to allow the individual to have an account;
   e. the service provider creating an account and providing the individual with a username and password;
   f. the service provider providing a medical information card to the individual;
   g. the individual providing his or her medical information to the service provider to be saved in a central database;
   h. the individual downloading the medical information from the central database and storing the medical information on the medical information card;
   i. the service provider detecting that the individual's vehicle has been involved in a crash;
   j. the service provider being provided with the location of the individual; and
   k. the service provider contacting emergency services to notify emergency service of the crash and the location of the vehicle.

2. The method of claim 1 further comprising steps of:
   a first responder locating the medical information card during an emergency; and
   the first responder reading the medical information stored on the medical information card using an electronic device.

3. The method of claim 1 wherein:
the location of the individual is provided via a global positioning system.

4. The method of claim 1 further comprising a step of:
the service provider directing emergency services to look for a medical emergency card at the location of the vehicle.

5. The method of claim 1 further comprising a step of:
the service provider providing medical information to the emergency services.

6. The method of claim 1 further comprising steps of:
the service provider being contacted by the individual and informed that the individual needs emergency services via an electronic device;
the service provider being provided with the location of the individual;
the service provider contacting emergency services to notify emergency service of the crash and the location of the vehicle.

7. The method of claim 1 wherein:
the location of the individual is provided via a global positioning system.

8. The method of claim 1 further comprising a step of:
the service provider directing emergency services to look for a medical emergency card at the location of the vehicle.

9. The method of claim 1 further comprising a step of:
the service provider providing medical information to the emergency services.

10. A system for using a medical information card for storing medical information and providing medical information to first responders comprising:
an individual creating an account with a service provider over the interne;
the individual providing the service provider with his or her contact information;
the service provider reviewing the contact information and rendering a decision on whether to allow the individual to have an account;
the service provider deciding to allow the individual to have an account;
the service provider creating an account and providing the individual with a username and password;
the service provider providing a medical information card to the individual;
the individual providing his or her medical information to the service provider;
the medical information being saved in a central database;
the individual downloading the medical information from the central database and storing the medical information on the medical information card;
the service provider detecting that the individual's vehicle has been involved in a crash;
the service provider being provided with the location of the individual; and
the service provider contacting emergency services to notify emergency service of the crash and the location of the vehicle.

11. The system of claim 10 further comprising:
a first responder locating the medical information card during an emergency; and
the first responder reading the medical information stored on the medical information card using an electronic device.

12. The system of claim 10 further comprising:
the location of the individual is provided via a global positioning system.

13. The system of claim 10 further comprising:
the service provider directing emergency services to look for a medical emergency card at the location of the vehicle.

14. The system of claim 10 further comprising:
the service provider providing medical information to the emergency services.

15. The system of claim 10 further comprising:
the service provider being contacted by the individual and informed that the individual needs emergency services via an electronic device;
the service provider being provided with the location of the individual;
the service provider contacting emergency services to notify emergency service of the crash and the location of the vehicle.

16. The system of claim 10 further comprising:
the location of the individual is provided via a global positioning system.

17. The system of claim 10 further comprising:
the service provider directing emergency services to look for a medical emergency card at the location of the vehicle.

18. The system of claim 10 further comprising:
the service provider providing medical information to the emergency services.

* * * * *